United States Patent [19]

Todd

[11] 4,455,141

[45] Jun. 19, 1984

[54] DRAINAGE APPARATUS WITH VACUUM CONTROL

[76] Inventor: Edward P. Todd, 3145 Warren Wood Wynd, Lexington, Ky. 40502

[21] Appl. No.: 386,241

[22] Filed: Jun. 8, 1982

[51] Int. Cl.$^3$ ............................................. A61M 1/00
[52] U.S. Cl. ..................................... 604/319; 604/321
[58] Field of Search ............... 604/317, 318, 319, 321, 604/323, 324; 137/205; 433/91

[56] References Cited

U.S. PATENT DOCUMENTS

| 3,861,390 | 1/1975 | Schachet | 604/321 |
| 4,018,224 | 4/1977 | Kurtz et al. | 604/321 |
| 4,261,362 | 4/1981 | Kurtz et al. | 604/320 |
| 4,289,158 | 9/1981 | Nehring | 137/205 |
| 4,324,244 | 4/1982 | Kurtz et al. | 604/321 |

FOREIGN PATENT DOCUMENTS 63907   11/1982   European Pat. Off. ............ 604/321

Primary Examiner—C. Fred Rosenbaum
Assistant Examiner—J. L. Kruter
Attorney, Agent, or Firm—Frank C. Leach, Jr.

[57] ABSTRACT

A drainage apparatus has a collection chamber connected to the pleural cavity of a patient with a vacuum pump connected through a water seal chamber to the collection chamber. A pressure regulating chamber maintains the negative pressure created by the vacuum pump in the water seal chamber at a desired negative pressure. When there is an increase in negative pressure within the pleural cavity of the patient, atmospheric pressure is transmitted through a liquid at a selected level in an excess negativity chamber to the collection chamber to reduce the negative pressure in the collection chamber and the pleural cavity of the patient connected thereto to a selected maximum above the negative pressure maintained in the collection chamber by the vacuum pump and regulated by the pressure regulating chamber.

20 Claims, 20 Drawing Figures

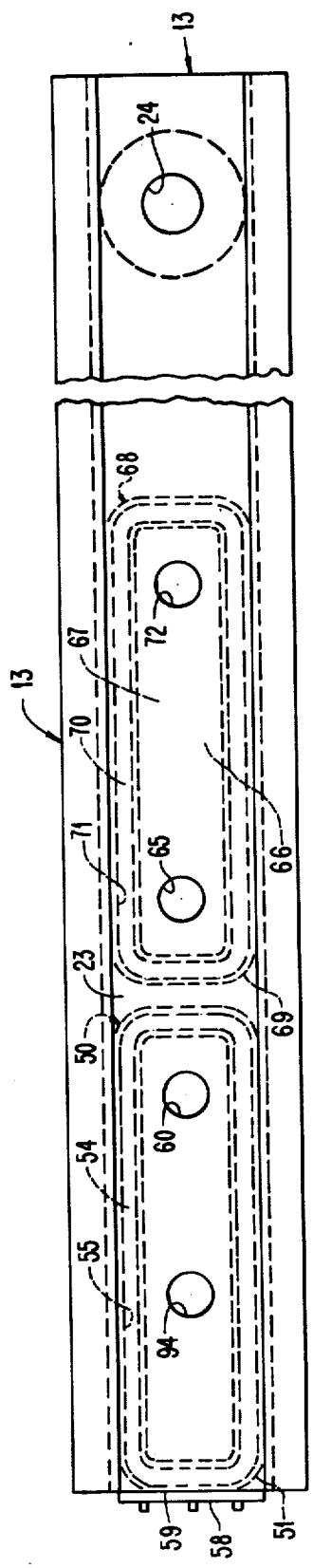
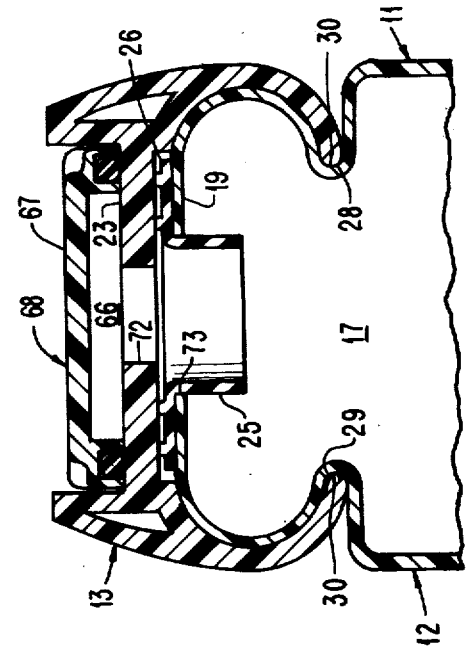
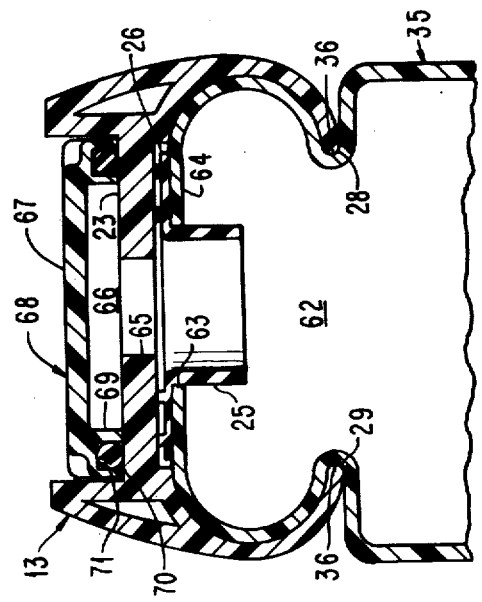
FIG.2
FIG.6
FIG.5

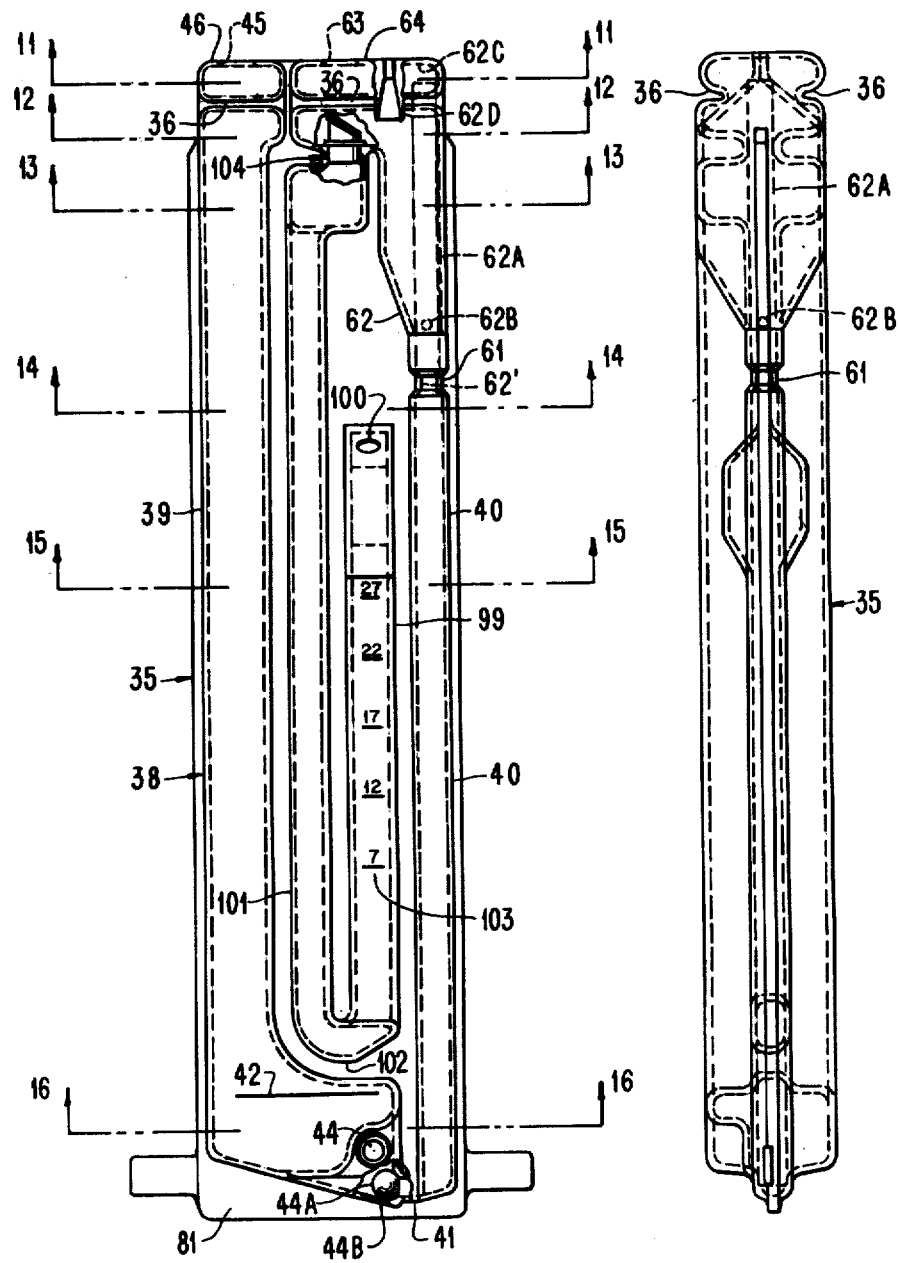

DRAINAGE APPARATUS WITH VACUUM CONTROL

This invention relates to a drainage apparatus for draining fluids from a body cavity and, more particularly, to a drainage apparatus for draining fluids from a pleural cavity of a body while maintaining a maximum negative pressure within the pleural cavity.

Various types of drainage apparatuses have been developed for use in draining fluids from the pleural cavity of a human being in a clean and aseptic environment. Examples of these drainage apparatuses are disclosed in U.S. Pat. No. 3,363,626 to Bidwell et al, U.S. Pat. No. 3,363,627 to Bidwell et al, U.S. Pat. No. 3,559,647 to Bidwell et al, U.S. Pat. No. 3,683,913 to Kurtz et al, U.S. Pat. No. 3,757,783 to Alley, U.S. Pat. No. 3,783,870 to Schachet, U.S. Pat. No. 3,853,128 to Kurtz et al, U.S. Pat. No. 3,924,624 to Schachet, U.S. Pat. No. 3,946,735 to DeWall, and U.S. Pat. No. 4,195,633 to Nehring et al.

The drainage apparatus of each of the aforesaid patents discloses an arrangement for draining fluids from the pleural cavity of a human being into a collection chamber maintained at a negative pressure. While the apparatuses of most of the aforesaid patents are capable of controlling the negative pressure in the collection chamber, which receives the fluids from the pleural cavity of the human being, so that a minimum predetermined negative pressure exists within the collection chamber, none of the apparatuses of the aforesaid patents has any arrangement for limiting an increase in negative pressure in the pleural cavity of a human being to any selected maximum when such occurs.

There are times when it is desired to increase the negative pressure within the pleural cavity of a human being for a short period of time. This is to cause break up of any blood clots in the pleural cavity, break up of any fibrin accumulation around the chest tube in the body, and break up of any materials collected within the tube leading from the pleural cavity of the human being to the collection chamber of the drainage apparatus. This increase in negative pressure in the pleural cavity can be accomplished through compressing and stripping the tube leading from the pleural cavity of the human being to the collection chamber of the drainage apparatus so as to produce a sudden increase in negative pressure while also causing the tube to be stripped of any materials therein so that they pass into the collection chamber of the drainage apparatus.

It is desired to be able to dissipate this excess negative pressure in the pleural cavity as soon as possible and within a relatively short period of time such as no more than three minutes, for example. If this excess negative pressure in the pleural cavity is not reduced within a relatively short period of time, this excess negative pressure in the pleural cavity can cause barotrauma to the lungs. This can result in an air leak in the lung or lungs exposed to this excess negative pressure to cause further medical complications of the person whose pleural cavity is connected to the collection chamber of the drainage apparatus.

One means of reducing the excess negative pressure in the pleural cavity would be to disconnect the tube, which is between the pleural cavity of the human being and the collection chamber of the drainage apparatus, to allow atmospheric air to enter the collection chamber. However, this air pressure could cause collapse of one or both of the lungs due to the transient evacuation of the negative pressure. Furthermore, this defeats the purpose of the drainage apparatus providing a clean and aseptic environment since the disconnection of the tube could result in contamination. Therefore, this disconnection of the tube is a totally unsatisfactory arrangement for reducing the excess negative pressure. Additionally, this disconnection of the tube would depend upon the attendant recognizing the time at which it is desired to reduce this excess negative pressure.

While the drainage apparatus of the aforesaid U.S. Pat. No. 3,683,913 to Kurtz et al includes a valve to permit development of a high negative pressure in the pleural cavity of a human being when the person is attempting to expand the lungs to make a strong respiratory effort to open a blockage in his or her bronchial tubes, for example, there is no way of relieving the increased negative pressure. That is, in the apparatus of the aforesaid U.S. Pat. No. 3,683,913 to Kurtz et al, the person, who is connected to the collection chamber of the drainage apparatus, must have a reduction in the negative pressure in the pleural cavity before the valve returns to its open position.

Thus, the drainage apparatus of the aforesaid U.S. Pat. No. 3,683,913 to Kurtz et al seems to increase the possibility of barotrauma in the lungs. This is because there is no means to dissipate the increased negative pressure in the pleural cavity; instead, it is maintained in the pleural cavity. Therefore, a prolonged exposure of the lungs to the excess negative pressure in the pleural cavity would appear to occur when using the drainage apparatus of the aforesaid U.S. Pat. No. 3,683,913 to Kurtz et al.

The drainage apparatus of the present invention satisfactorily solves the foregoing problem of allowing an increased negative pressure to be created within the pleural cavity of a person connected to the collection chamber of the drainage apparatus for a predetermined period of time with this period of time being sufficiently small so that the chance for barotrauma to the lungs of the person connected to the collection chamber of the drainage apparatus will be minimized. The drainage apparatus of the present invention limits the negative pressure in the pleural cavity to a predetermined or selected maximum above the selected negative pressure, which is produced within the collection chamber of the drainage apparatus by the combination of the vacuum pump and the pressure regulating chamber. Thus, the excess negative pressure in the pleural cavity of the person connected to the collection chamber of the drainage apparatus is limited so that the negative pressure does not become too large or exist for too long a period of time. This arrangement allows the negative pressure to be increased so that the tube from the pleural cavity to the collection chamber of the drainage apparatus can be stripped to produce a sudden increase in negative pressure in the pleural cavity to break up clots therein and to break up fibrin which have accumulated in or around the chest tube in the body.

However, the drainage apparatus of the present invention does not allow this excess negative pressure to exist for a period of time in which there can be damage to the lungs. Therefore, the drainage apparatus of the present invention not only enables the negative pressure in the pleural cavity to be increased when desired through stripping the tube, which connects the pleural cavity to the collection chamber of the drainage apparatus, but also insures that this negative pressure does not remain for an undesirable period of time.

Additionally, if the negative pressure in the pleural cavity of the person connected to the collection chamber of the drainage apparatus should increase for any reason, this excess negative pressure is dissipated by the arrangement used in the drainage apparatus of the present invention. Thus, constant monitoring of the patient is not necessary to ascertain if there is excess negative pressure in the patient's pleural cavity.

While the drainage apparatus of the aforesaid U.S. Pat. No. 3,363,627 to Bidwell et al discloses a reservoir to collect liquid to recognize when there has been an excess negative pressure in the pleural cavity of the person connected to the collection chamber of the drainage apparatus, this may not be recognized until damage has been done to the lungs of the patient. That is, the reservoir might not be inspected until the next morning as is mentioned in the aforesaid U.S. Pat. No. 3,363,627 to Bidwell et al. By this time, substantial damage may have been done to the lungs of the patient.

This problem is avoided by the drainage apparatus of the present invention. This is because the drainage apparatus of the present invention does not allow the negative pressure in the pleural cavity to remain above a predetermined or selected maximum above the negative pressure produced in the collection chamber of the drainage apparatus by the vacuum source beyond a predetermined period of time.

An object of this invention is to provide a unique drainage apparatus.

Another object of this invention is to provide a drainage apparatus for reducing excess negative pressure in a pleural cavity being drained by the drainage apparatus.

A further object of this invention is to provide a drainage apparatus in which a predetermined or selected maximum negative pressure can occur in the pleural cavity having fluids in the pleural cavity drained by the drainage apparatus without damage to the lungs.

Still another object of this invention is to provide a drainage apparatus in which the physician can select a negative pressure range that the physician deems desirable.

A still further object of this invention is to provide a drainage apparatus in which the negative pressure can be maintained within a narrow range.

Other objects of this invention will be readily perceived from the following description, claims, and drawings.

This invention relates to a drainage apparatus including collection means having inlet means for communication with the pleural cavity of a body to receive fluids therefrom. A first selected negative pressure is created within the collection means by vacuum means to normally maintain the pleural cavity communicating with the inlet means at the first selected negative pressure. The vacuum means removes from the collection means gases of the fluids received in the collection means from the pleural cavity communicating with the inlet means of the collection means. Gas preventing return means between the collection means and the vacuum means prevents return of the gases to the collection means after being removed therefrom by the vacuum means. The negative pressure within the collection means is controlled by control means to a second higher negative pressure above the first negative pressure when created by the vacuum means the negative pressure within the collection means is increased.

The attached drawings illustrate preferred embodiments of the invention, in which:

FIG. 1A is an end elevational view of the drainage apparatus of FIG. 1;

FIG. 2 is a bottom plan view of a header of the modular configuration of the drainage apparatus of FIG. 1 and taken along line 2—2 of FIG. 1;

FIG. 5 is a fragmentary sectional view of the drainage apparatus of FIG. 1 taken along line 5—5 of FIG. 1 and showing the liquid seal chamber communicating with a second sealed chamber;

FIG. 6 is a fragmentary sectional view of the drainage apparatus of FIG. 1 taken along line 6—6 of FIG. 1 and showing the collection chamber communicating with the second sealed chamber;

FIG. 8 is a front elevational view, partly in section, of one of the three bodies forming the modular configuration of the drainage apparatus of FIG. 1 and including the arrangement for preventing excess negative pressure within the pleural cavity of a patient connected to the drainage apparatus;

FIG. 9 is an end elevational view of the body of FIG. 8;

FIG. 10 is a top plan view of the body of FIG. 8;

Figure 1:
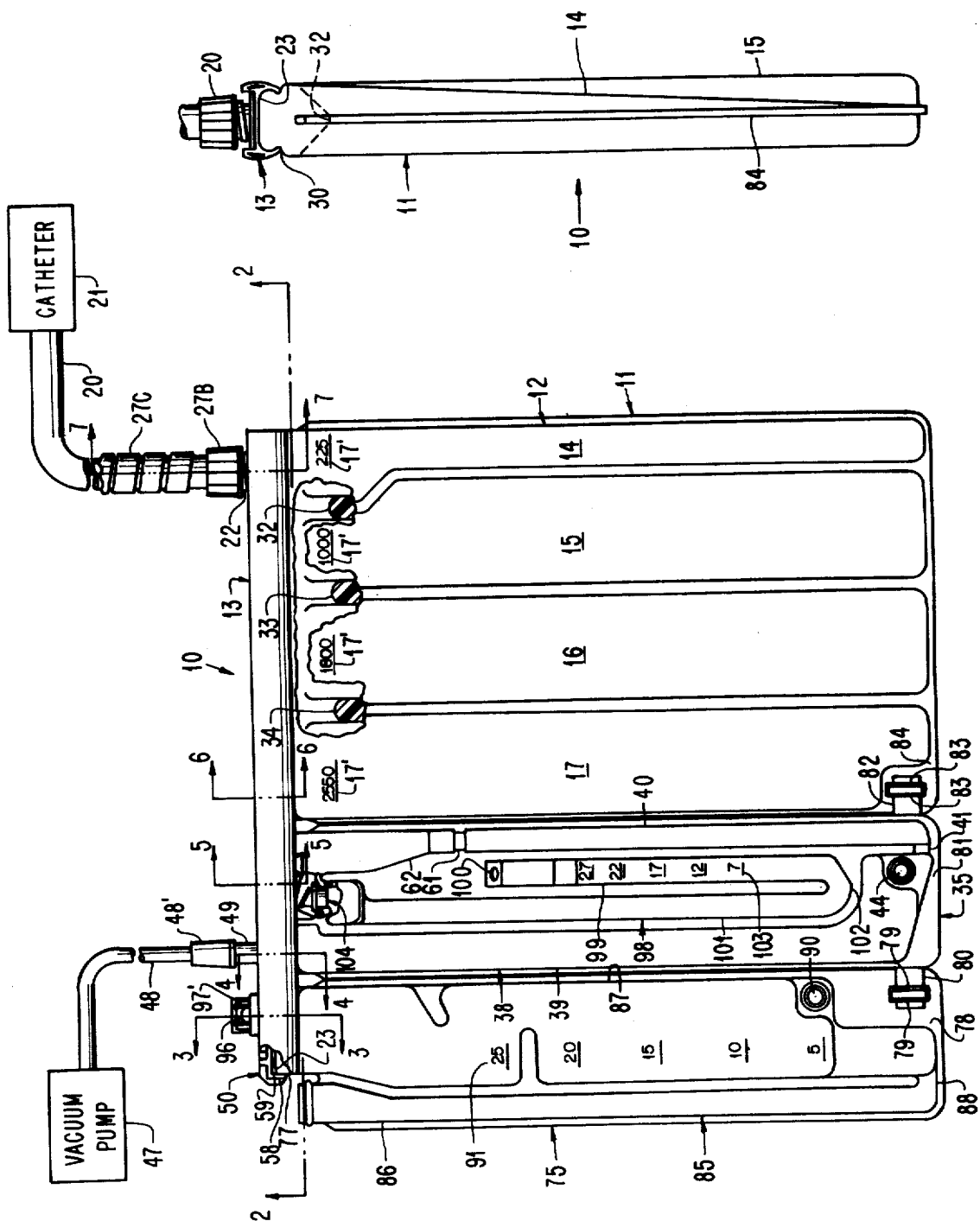
FIG. 1 is a front elevational view, partly schematic, of the drainage apparatus of the present invention.

Referring to the drawings and particularly FIG. 1, there is shown a drainage apparatus 10 for draining fluids from the pleural cavity of a patient. The drainage apparatus 10 has a modular configuration with this modular configuration being the invention of Eugene E. Weilbacher as claimed in this copending patent application for "Modular Apparatus," Ser. No. 386,242, filed June 8, 1982.

The drainage apparatus 10 includes a first transparent plastic body or unit 11 having a collection or trap chamber 12 for receiving fluids from the pleural cavity of the patient. The first body or unit 11 is supported by a header 13, which functions as support means for the body or unit 11, and is preferably a non-transparent plastic.

The collection chamber 12 is divided into four compartments 14, 15, 16, and 17. The compartment 14 is much smaller than each of the compartments 15, 16, and 17 so that it may be used as a special pediatric compartment to accurately measure the quantity of liquids in the fluids obtained from the pleural cavity of a child when the drainage apparatus 10 is used with a child so as to maximize the accuracy of the determination of fluid loss.

The compartment 14 holds 225 cc of liquids. The compartment 15 retains 775 cc of liquids. The compartment 16 holds 800 cc of liquids, and the compartment 17 retains 750 cc of liquids. Thus, the compartments 14–17 can hold a total volume of 2550 cc of liquids. Each of the compartments 14–17 has idicia 17' to indicate the total volume of liquids collected in the collection chamber 12.

Figure 7:
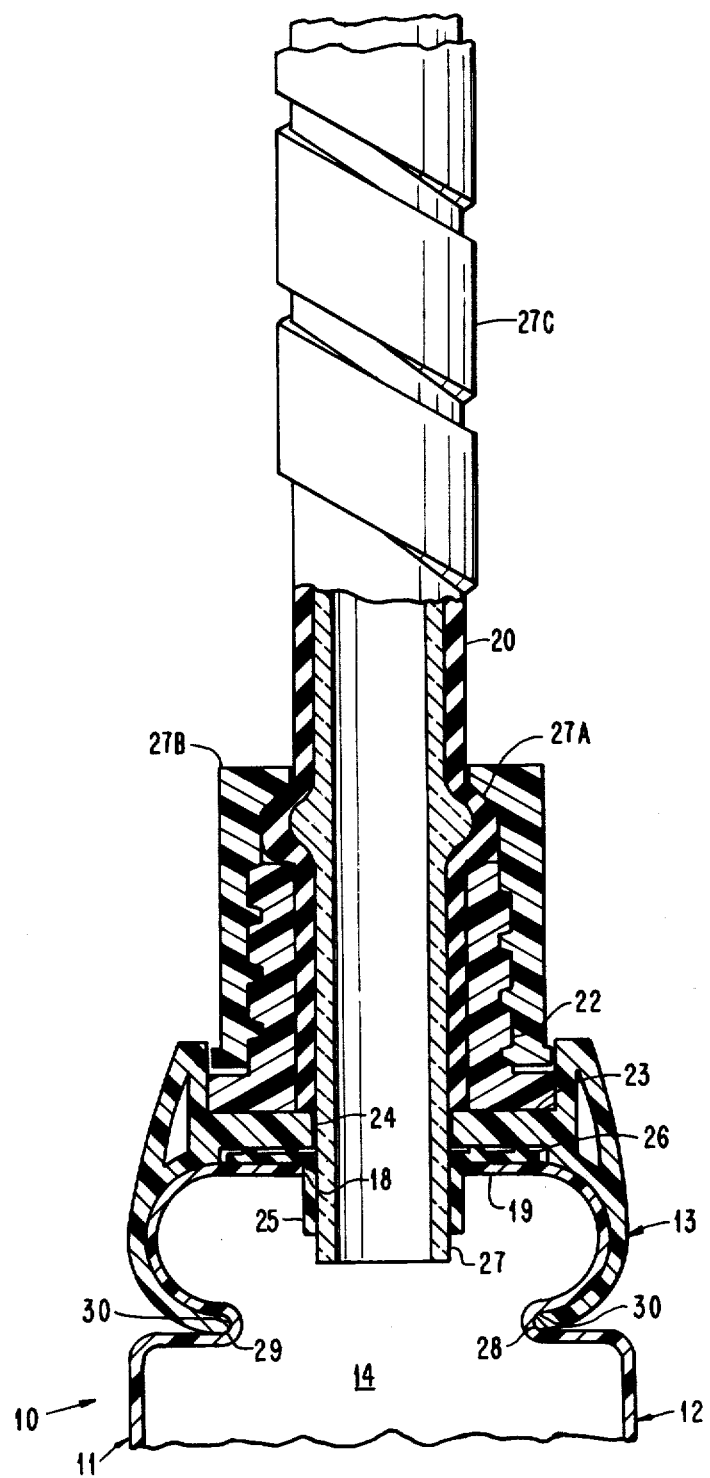
FIG. 7 is a fragmentary sectional view of the drainage apparatus of FIG. 1 taken along line 7—7 of FIG. 1 and showing the collection chamber communicating with a hose leading to the pleural cavity of a patient.

The collection chamber 12 has an inlet 18 (see FIG. 7) in its substantially horizontal upper wall 19 above the compartment 14, which is the pediatric compartment. Thus, the liquids from the fluids obtained from the pleural cavity of any patient connected to the drainage apparatus 10 are initially collected in the compartment 14.

The inlet 18 of the collection chamber 12 communicates with the pleural cavity of a patient through a flexible tube 20 (see FIG. 1). The tube 20 has one end connected to the pleural cavity of the patient through a catheter 21, for example, and its other end extending into a hollow fitting 22, which is fixed to the upper surface of a horizontally extending wall 23 (see FIG. 7) of the header 13 and has threads on its outer surface.

The horizontally extending wall 23, which extends for the length of the header 13, has a circular passage 24 extending therethrough and communicating with the inlet 18 in the upper wall 19 of the collection chamber 12. A gasket 25, which is formed of a suitable elastomeric material such as nitrile rubber, for example, is disposed within the inlet 18 and has an annular flange 26 abutting against the bottom surface of the wall 23 of the header 13 and surrounding the bottom end of the passage 24 in the wall 23 of the header 13 so as to form a seal therewith whereby the fluids from the pleural cavity of the patient will flow into the compartment 14 of the collection chamber 12.

The flexible tube 20 has a translucent plastic tube 27 disposed in its lower end and extending through the passage 24 in the wall 23 of the header 13 and the interior of the gasket 25 to communicate with the interior of the compartment 14. The extension of the tube 27 into the compartment 14 is controlled by a projection 27A on the flexible tube 20 abutting the upper surface of the fitting 22.

A threaded cap 27B, which has threads on its inner surface cooperating with the threads on the outer surface of the fitting 22, pushes the projection 27A into engagement with the upper surface of the fitting 22 to retain the flexible tube 20 within the hollow fitting 22. This also produces a seal to prevent any leakage of air into the compartment 14.

The outer surface of the portion of the tube 20 adjacent the upper end of the tube 27 has an element 27C, which is formed of a suitable translucent plastic, wrapped therearound and fitting firmly so as to not be mobile. The element 27C prevents any kinking of the flexible tube 20.

The header 13 has its support edges 28 and 29 disposed within slots or grooves 30 formed in the exterior of the upper end of the body 11 on opposite sides thereof to enable the header 13 to support the body 11. Thus, the annular flange 26 of the gasket 25 is held against the bottom surface of the horizontally extending wall 23 of the header 13 to form the seal between the passage 24 in the wall 23 and the inlet 18 in the upper wall 19 of the body 11.

As shown in FIG. 1, the upper end of the compartment 14 of the collection chamber 12 communicates with the upper end of the compartment 15 of the collection chamber 12 by a V-shaped channel or passage 32. Thus, when the compartment 14 becomes filled with liquids so that the compartment 14 has 225 cc of liquids therein, the liquids flow into the compartment 15 through the channel or passage 32.

The upper end of the compartment 15 of the collection chamber 12 communicates through a V-shaped channel or passage 33 with the upper end of the compartment 16. Accordingly, when the compartments 14 and 15 become filled with liquids so that the compartments 14 and 15 have a total of 1000 cc of liquids therein, the liquids enter the compartment 16 through the channel or passage 33.

The upper end of the compartment 16 of the collection chamber 12 communicates with the upper end of the compartment 17 of the collection chamber 12 through a V-shaped channel or passage 34. Therefore, when the compartment 16 becomes filled with liquids so that the compartments 14, 15, and 16 have a total of 1800 cc of liquids therein, the liquids flow into the compartment 17 through the channel or passage 34.

The header 13 supports a second body or unit 35 adjacent the first body 11. The second body 35 has a pair of slots or grooves 36 (see FIG. 5) formed in its exterior on opposite sides thereof adjacent its upper end to receive the edges 28 and 29 of the header 13.

Figure 14:
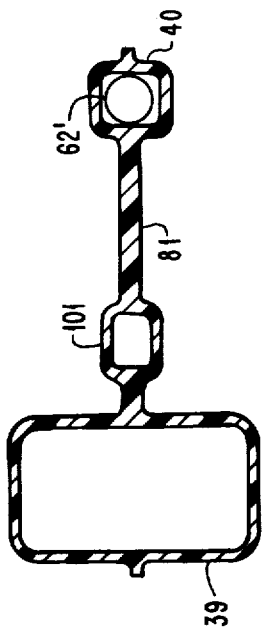
FIG. 14 is a sectional view of the body of FIG. 8 and taken along line 14—14 of FIG. 8.
Figure 15:
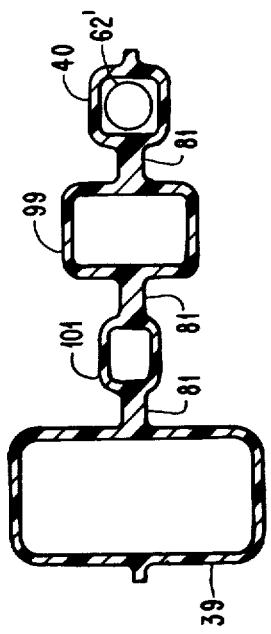
FIG. 15 is a sectional view of the body of FIG. 8 and taken along line 15—15 of FIG. 8.
Figure 16:
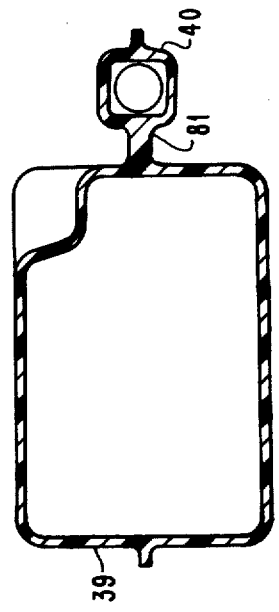
FIG. 16 is a sectional view of the body of FIG. 8 and taken along line 16—16 of FIG. 8.
Figure 11:
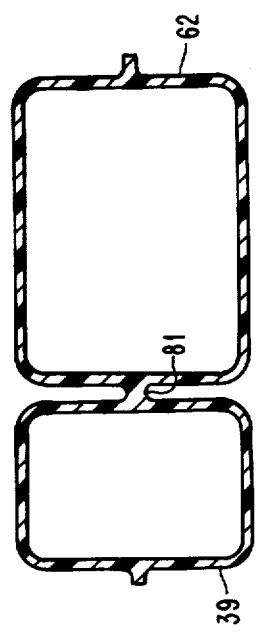
FIG. 11 is a sectional view of the body of FIG. 8 and taken along line 11—11 of FIG. 8.
Figure 12:
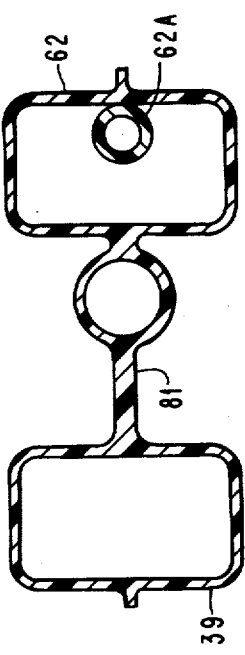
FIG. 12 is a sectional view of the body of FIG. 8 and taken along line 12—12 of FIG. 8.
Figure 13:
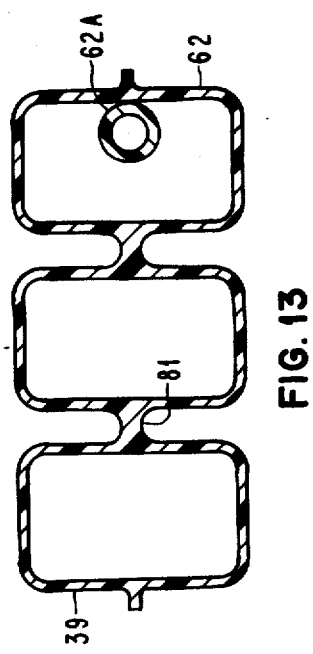
FIG. 13 is a sectional view of the body of FIG. 8 and taken along line 13—13 of FIG. 8.

The body 35 (see FIGS. 1 and 8) includes a liquid seal chamber 38. The liquid seal chamber 38 includes a first column 39 and a second column 40. The relationships of the cross sectional areas of the columns 39 and 40 are shown in FIGS. 14 to 16.

The columns 39 and 40 communicate with each other at their bottom ends through a passage 41 so that the liquid seal chamber 38 is substantially U-shaped. Liquid such as water, for example, spans the bottom of the two columns 39 and 40 and extends to a level line 42 as shown in FIG. 8. The liquid such as water, for example, is added to the columns 39 through 40 through a Luer valve 44 (see FIG. 1) in a wall of the liquid seal chamber 38 by adding water to the level line 42 (see FIG. 8).

A ball valve 44A is disposed in the lowermost portion of the first column 39 for cooperation with a valve seat 44B formed by the end of the passage 41 communicating with the bottom of the first column 39. The ball valve 44A does not completely prevent flow of liquid from the first column 39 to the second column 40 but retards flow so that there is no sudden evacuation of the liquid from the liquid seal chamber 38 to the collection chamber 12 (see FIG. 1). The ball valve 44A (see FIG. 8) also prevents large bubbles from flowing to the second column 40 to reduce the possibility of liquid flowing therewith.

Figure 4:
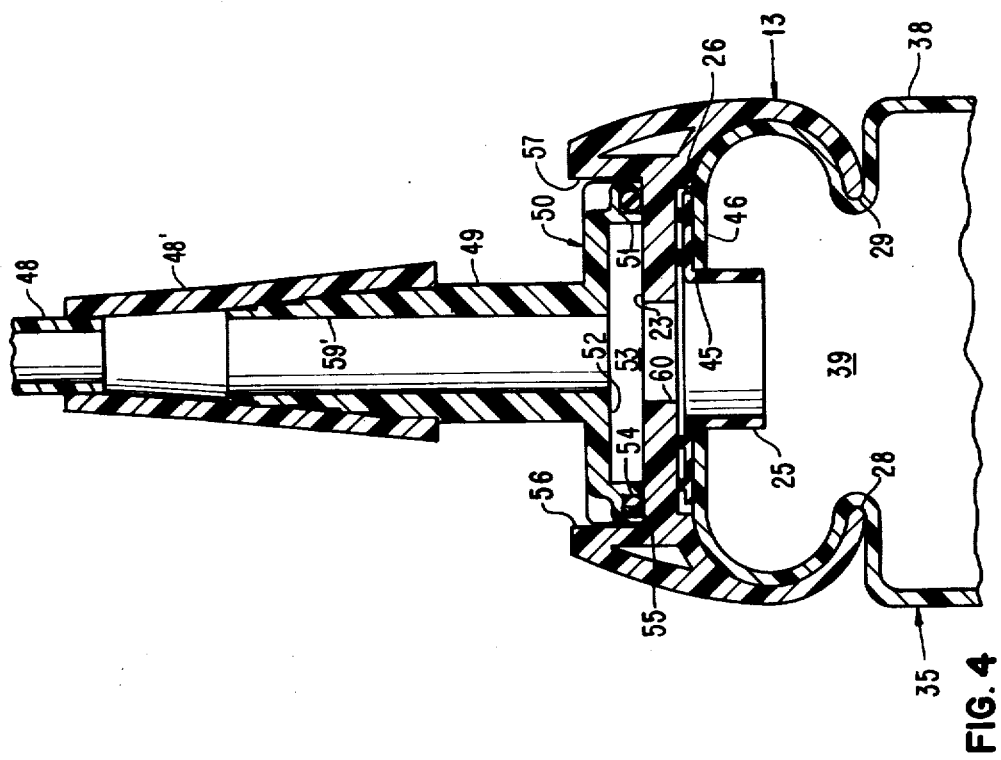
FIG. 4 is a fragmentary sectional view of the drainage apparatus of FIG. 1 taken along line 4—4 of FIG. 1 and showing the vacuum pump and the liquid seal chamber communicating with the same sealed chamber.

The first column 39 of the liquid seal chamber 38 has a circular inlet 45 (see FIG. 10) formed in its upper wall 46 for communication with a negative pressure source such as a vacuum pump 47 (see FIG. 1), for example, by a tube 48. The tube 48 is connected by a fitting 48' to a tapered and stepped hollow connector 49, which is formed integral with a manifold plate 50 (see FIGS. 2 and 4).

The manifold plate 50 is supported on the upper surface of the wall 23 of the header 13 and is fixed thereto by any suitable adhesive or bonding means. The manifold plate 50 has a peripheral projection 51 (see FIG. 4) extending downwardly to space a horizontally extending wall 52 of the manifold plate 50 from the upper surface of the wall 23 of the header 13 to form a chamber 53 therebetween. A sealing ring 54 is supported in a peripheral groove 55 in the peripheral projection 51 of the manifold plate 50 to form a seal with the upper surface of the wall 23 of the header 13.

The position of the manifold plate 50 on the header 13 is controlled by disposing the manifold plate 50 between a pair of upstanding walls 56 and 57 of the header 13. The longitudinal position of the manifold plate 50 is controlled by a flange 58 (see FIGS. 1 and 2) on one end of the manifold plate 50 bearing against an end 59 (see FIG. 2) of the wall 23.

As a result, the hollow connector 49 (see FIG. 4) has its passage 59' aligned with a circular passage 60 extending through the wall 23 of the header 13. The passage 60 communicates with the inlet 45 in the upper wall 46 of the first column 39 of the liquid seal chamber 38. The inlet 45 has one of the gaskets 25 disposed therein to form a seal with the passage 60 in the wall 23 of the header 13. Accordingly, the vacuum pump 47 (see FIG. 1) exerts a negative pressure within the chamber 53 (see FIG. 4) and the first column 39 (see FIGS. 1 and 8) of the liquid seal chamber 38.

The second column 40 of the liquid seal chamber 38 has its upper end 61 terminating in the lower end of a reservoir 62 through a reduced circular opening 62' (see FIG. 8) to reduce the rate of liquid flowing therethrough. The reservoir 62 has a vertically disposed bypass tube 62A extending upwardly therein from the reduced circular opening 62'. The tube 62A has holes 62B adjacent its lower end and is open at its upper end to provide communication from the interior of the tube 62A to the interior of the reservoir 62.

This structure prevents loss of any of the liquid from the liquid seal chamber 38 through the reservoir 62 to the collection chamber 12 (see FIG. 1), which is in communication with the reservoir 62 as will be explained hereinafter, when a patient gasps strongly. If a sufficient quantity of the liquid in the liquid seal chamber 38 were removed therefrom by the patient gasping strongly, atmospheric pressure could enter the pleural cavity of the patient if the vacuum pump 47 were disconnected.

When a patient gasps strongly to create a relatively high negative pressure within the patient's pleural cavity, liquid is initially rapidly drawn up the second column 40 (see FIG. 8) of the liquid seal chamber 38 and into the reservoir 62 through the holes 62B and the open upper end of the tube 62A. This rapid and sufficiently higher negativity within the pleural cavity of the patient transfers the liquid in the liquid seal chamber 38 into the reservoir 62.

However, the open upper end of the tube 62A is not blocked by the liquid sucked into the reservoir 62. As a result, air and liquid can flow through the open upper end of the tube 62A into the reservoir 62 for transmittal of air through the collection chamber 12 (see FIG. 1) to the pleural cavity of the patient. When the flow of air up the tube 62A (see FIG. 8) ceases, the liquid in the reservoir 62 immediately drains therefrom through the holes 62B in the tube 62A and down the second column 40 of the liquid seal chamber 38 to again establish the liquid seal in the liquid seal chamber 38. Thus, no liquid is lost from the liquid seal chamber 38.

It should be understood that liquid also passes through the open upper end of the tube 62A and engages a substantially horizontal wall 62C of the reservoir 62. This liquid is retained within the reservoir 62 by a substantially vertical wall 62D so that none of the liquid can escape through an opening 63 (see FIG. 10) in upper wall 64 of the reservoir 62.

The opening 63 communicates with a circular passage 65 (see FIG. 5) extending through the wall 23 of the header 13. The opening 63 has one of the gaskets 25 disposed therein to form a seal between the opening 63 and the passage 65.

The passage 65 in the wall 23 of the header 13 communicates with a chamber 66, which is formed between the wall 23 and a horizontally extending wall 67 of a manifold plate 68. The manifold plate 68 is secured to the wall 23 in the same manner as the manifold plate 50.

The manifold plate 68 has a peripheral projection 69 bearing against the upper surface of the wall 23 to space the wall 67 of the manifold plate therefrom. The peripheral projection 69 has a sealing ring 70 mounted in a peripheral groove 71 in the peripheral projection 69 to seal the chamber 66. The manifold plate 68 is longitudinally positioned on the upper surface of the wall 23 of the header 13 so that the sealed chamber 66 also communicates with a circular passage 72 (see FIG. 6) extending through the wall 23. Thus, the passages 65 (see FIG. 5) and 72 (see FIG. 6) communicate with each other through the sealed chamber 66 so that the sealed chamber 66 functions as passage or communicating means.

The passage 72 is aligned with a circular outlet opening 73 in the upper wall 19 of the collection chamber 12. The outlet opening 73 has one of the gaskets 25 mounted therein to form a seal between the outlet opening 73 and the passage 72. Therefore, the reservoir 62 (see FIG. 1) communicates with the collection chamber 12 above the compartment 17 via the sealed chamber 66 (see FIG. 6).

Thus, the second column 40 (see FIG. 1) of the liquid seal chamber 38 is in communication with the collection chamber 12. Accordingly, any vacuum produced in the liquid seal chamber 38 by the vacuum pump 47 and regulated in a manner to be hereinafter described is created in the collection chamber 12 so that this same negative pressure exists within the pleural cavity of the patient connected to the collection chamber 12 of the drainage apparatus 10 by the tube 20.

A third body or unit 75 also is supported on the header 13. The body 75 has slots or grooves 76 (see FIG. 3) adjacent its upper end on its exterior to receive the edges 28 and 29 of the header 13. The body 75 has an end portion 77 (see FIG. 1) abutting the flange 58 of the manifold plate 50 (see FIG. 2), which is fixed to the header 13, to position the body 75 (see FIG. 1) on the header 13.

The third body 75 has a small portion of the lower end of its common connecting wall 78 punched or pushed out to form a pair of slots 79 to receive a tab 80 integrally formed on the lower end of a common connecting wall 81 of the second body 35. The reception of the tab 80 in the slots 79 joins the bodies 35 and 75 to each other at their lower ends with the adjacent edges of the walls 78 and 81 abutting.

The common connecting wall 81 of the second body 35 has a second tab 82 formed integral therewith on its lower end on the opposite end from the tab 80. The second tab 82 is disposed within slots 83, which are formed by punching or pushing out a small portion of a common connecting wall 84 of the first body 11. The disposition of the second tab 82 in the slots 83 joins the bodies 11 and 35 to each other at their lower ends with the walls 81 and 84 abutting.

It should be understood that the bodies 11, 35, and 75 are connected at their upper ends to the header 13 through the edges 28 (see FIG. 7) and 29 of the header 13 being disposed in the grooves 30, 36 (see FIG. 5), and 76 (see FIG. 3) in the bodies 11 (see FIG. 1), 35, and 75, respectively. The bodies 11, 35, and 75 are retained in position on the header 13 through the end portion 77 of the body 75 abutting the flange 58 of the manifold plate 50 (see FIG. 2) and the tube 27 (see FIG. 7) being disposed in the inlet 18 of the upper wall 19 of the first body 11. Thus, removal of the tube 27 enables easy replacement of the first body 11 when it is desired to replace the collection chamber 12.

The third body 75 (see FIG. 1) has a pressure regulating chamber 85, which controls the negative pressure applied by the vacuum pump 47 to the collection chamber 12. The pressure regulating chamber 85 includes a first column 86, which has its upper end open to communicate with the atmosphere, and a second column 87, which has a substantially larger cross sectional area than the first column 86. A passage 88 connects the bottom ends of the columns 86 and 87 to each other so that the pressure regulating chamber 85 is substantially U-shaped.

A liquid such as water, for example, is supplied to the passage 88 through a Luer valve 90 in the wall of the pressure regulating chamber 85 and spans the bottoms of the columns 86 and 87. The height of the liquid in the second column 87 controls the negative pressure produced by the vacuum pump 47 in the collection chamber 12. The column 87 has indicia 91 thereon to indicate the level at which the liquid is to be disposed in the second column 87 to have the desired negative pressure produced in the collection chamber 12 by the vacuum pump 47.

The second column 87 has a circular outlet opening 92 (see FIG. 3) in its upper wall 93 in alignment with a circular passage 94 extending through the wall 23 of the header 13. The outlet opening 92 has one of the gaskets 25 disposed therein to form a seal between the opening 92 and the passage 94.

The passage 94 in the wall 23 of the header 13 communicates with the chamber 53. As previously mentioned, the chamber 53 has the vacuum pump 47 (see FIG. 1) connected thereto in addition to having the first column 39 of the liquid seal chamber 38 communicating therewith. Thus, the chamber 53 (see FIG. 3) functions as passage or communicating means.

Accordingly, when the vacuum pump 47 (see FIG. 1) is producing a negative pressure in the collection chamber 12, atmospheric air flows through the liquid spanning the bottom ends of the columns 86 and 87 of the pressure regulating chamber 85 to the chamber 53 (see FIG. 3) to insure that the vacuum pump 47 (see FIG. 1) does not create a negative pressure beyond that selected. Thus, the level of the liquid in the second column 87 controls the selected negative pressure.

The wall 52 (see FIG. 3) of the manifold plate 50 has a circular outlet opening 95 communicating with the atmosphere. The outlet opening 95 is normally closed by a ball check valve 96, which is disposed within a cage 97 having a plurality of openings 97'. This cage 97 is secured to an annular projection 97A on the wall 52 of the manifold plate 50 by any suitable adhesive or bonding means.

Figure 3:
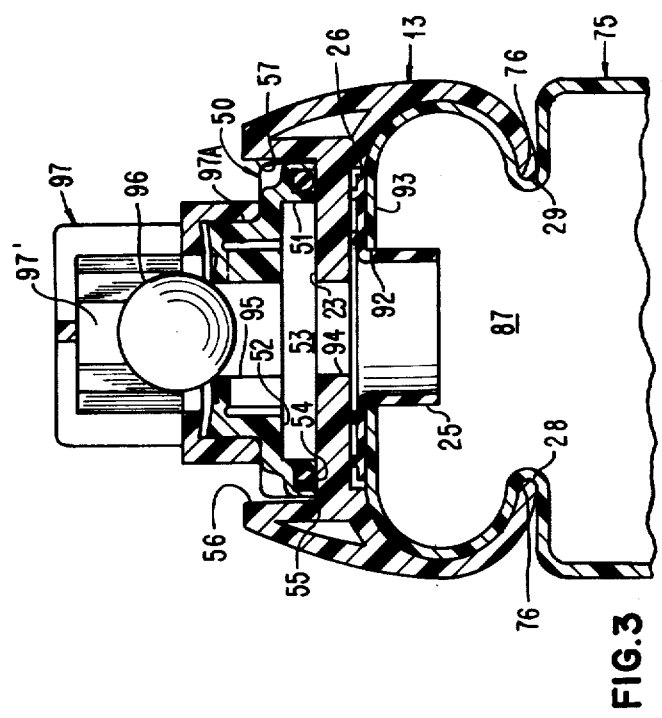
FIG. 3 is a fragmentary sectional view of the drainage apparatus of FIG. 1 taken along line 3—3 of FIG. 1 and showing the positive pressure relief valve and the pressure regulating chamber communicating with the same sealed chamber.

Accordingly, if the pressure in the collection chamber 12 (see FIG. 1) increases beyond atmospheric pressure and the pressure necessary to cross the liquid seal chamber 38, this increased pressure is vented through the liquid seal chamber 38 to the chamber 53 (see FIG. 3). This increased positive pressure is then vented to the atmosphere by the ball check valve 96 moving to an open position.

The body 35 (see FIG. 1) has an excess negativity chamber 98 formed therein. The excess negativity chamber 98 is utilized to limit the excess negative pressure in the collection chamber 12 and the pleural cavity of the patient connected to the tube 20 to a predetermined or selected maximum negative pressure greater than the negative pressure produced in the collection chamber 12 by the vacuum pump 47 in conjunction with the pressure regulating chamber 85 in a predetermined period of time. The selected maximum negative pressure is preferably two centimeters of water greater than the pressure selected in the pressure regulating chamber 85 with the predetermined period of time being preferably no more than three minutes.

The excess negativity chamber 98 is a U-shaped tube having a first leg or column 99 with its upper end communicating with the atmosphere through an opening 100 and a second leg or column 101 with its upper end communicating with the reservoir 62. The bottom ends of the legs or columns 99 and 101 are connected by a passage 102. A liquid, such as water, for example, is supplied through the opening 100 to span the bottom ends of the legs or columns 99 and 101.

The leg or column 99 has indicia 103 thereon to indicate the level to which the liquid is to be disposed in the leg or column 99. This level is selected in conjunction with the level of the liquid in the second column 87 of the pressure regulating chamber 85 to determine the selected maximum excess negative pressure. For example, if the second column 87 of the pressure regulating chamber is set at twenty-five centimeters of water, then the column 99 is filled to twenty-seven centimeters of water.

Figure 18:
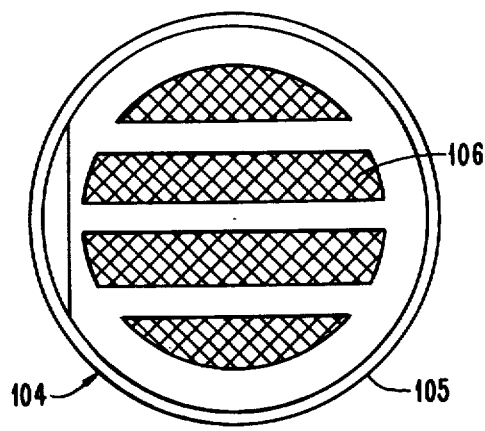
FIG. 18 is a top plan view of the flow control vent means of FIG. 17.
Figure 17:
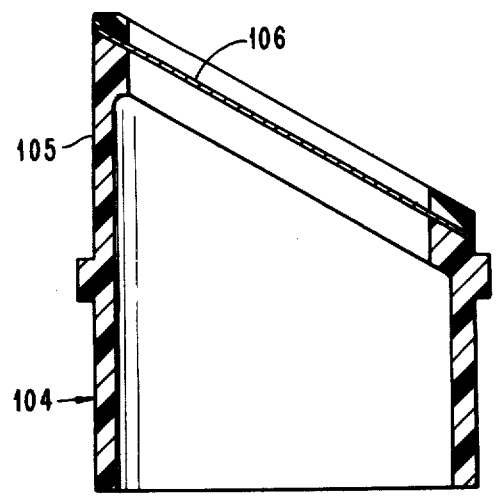
FIG. 17 is a sectional view of a flow control vent means used in controlling the excess negative pressure.

The upper end of the second leg or column 101 communicates with the reservoir 62 through flow control vent means 104 to the reservoir 62. As shown in FIGS. 17 and 18, the flow control vent means 104 includes a body 105, which is formed of a suitable plastic, having a filter 106 supported therein and through which the second leg or column 101 (see FIGS. 1 and 8) of the excess negativity chamber 98 communicates with the reservoir 62.

The material of the filter 106 (see FIGS. 17 and 18) is any suitable material capable of preventing the flow of liquid while allowing the flow of gas therethrough at a desired flow rate so as to function as a liquid check valve. Suitable examples of the material of the filter 106 of the flow control vent means 104 when the liquid is water are sold by Gelman Sciences, Ann Arbor, Michigan under the trademarks Acropor and Versapor.

Accordingly, the flow control vent means 104 prevents the liquid within the excess negativity chamber 98 (see FIG. 1) from flowing to the collection chamber 12 when there is a relatively high negative pressure existing in the pleural cavity of the patient connected to the collection chamber 12 through the tube 20 while still allowing flow of air at a selected flow rate in accordance with the porosity of the material of the filter 106 (see FIGS. 17 and 18) with this flow rate determining the period of time required to limit the excess negative pressure to the selected maximum.

It should be understood that the flow control vent means 104 results in the reduction of excess negativity by air flow through the excess negativity chamber 98 (see FIG. 1) being relatively slow so as not to be able to compensate for the strong gasp of a patient to avoid the possible loss of the liquid from the liquid seal chamber 38. Accordingly, the rate and mechanism of a patient's gasp is such that the excess negativity chamber 98 and the flow control vent means 104 could not always function in time to prevent the loss of liquid from the liquid seal chamber 38 without the bypass tube 62A (see FIG. 8).

Considering the operation of the drainage apparatus 10 (see FIG. 1) with the tube 20 connected to the pleural cavity of the patient and the vacuum pump 47 connected to the liquid seal chamber 38, the vacuum pump 47 produces a desired negative pressure in the collection chamber 12 in accordance with the height of the liquid in the second column 87 of the pressure regulating chamber 85. For example, the negative pressure could be twenty-five centimeters of water.

If the negative pressure in the pleural cavity of the patient increases beyond that produced by the vacuum pump 47 in conjunction with the pressure regulating chamber 85, any increase in this negative pressure beyond the predetermined or selected maximum, as determined by the level of the liquid in the first leg or column 99 of the excess negativity chamber 98, results in atmospheric air flowing from the opening 100 through the liquid in the excess negativity chamber 98 into the collection chamber 12. Thus, the increase in the negative pressure in the pleural cavity of the patient connected to the tube 20 is limited. The flow rate of the air is controlled by the porosity of the material of the filter 106 (see FIGS. 17 and 18) of the flow control vent means 104.

Figure 19:
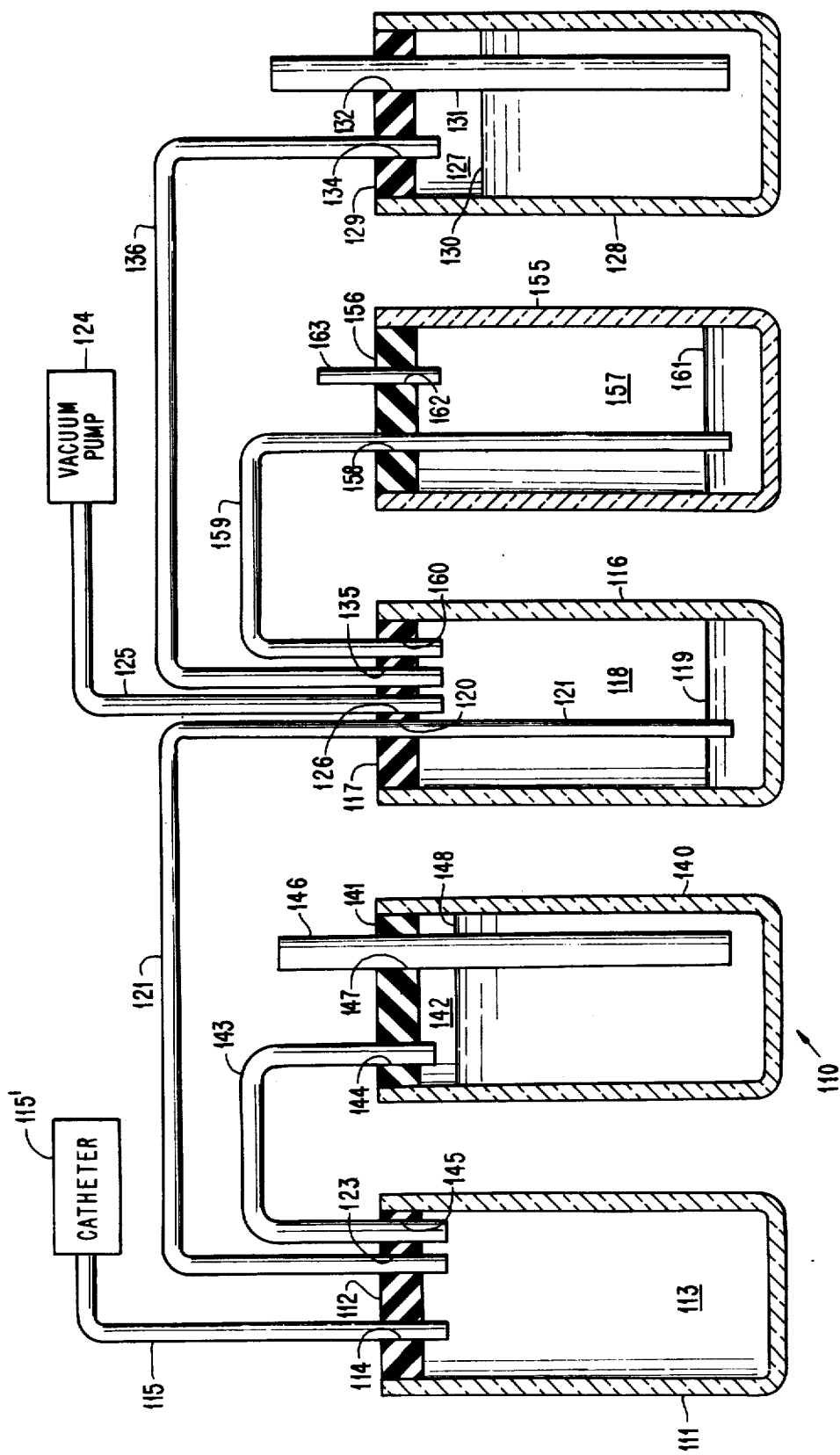
FIG. 19 is a schematic view of another embodiment of the drainage apparatus of the present invention.

Referring to FIG. 19, there is shown a drainage apparatus 110 for draining fluids from the pleural cavity of a patient. The drainage apparatus 110 includes a container 111 having a cover 112 to seal the interior of the container 111 to form a collection or trap chamber 113 therein for receiving fluids from the pleural cavity of the patient. The cover 112 has a port 114 communicating through a tube 115 and a catheter 115' with the pleural cavity of a patient. Accordingly, fluids from the pleural cavity of the patient, who is connected to the catheter 115', can flow into the collection chamber 113.

The drainage apparatus 110 includes a container 116 having a cover 117 to seal the interior of the container 116 to form a liquid seal chamber 118 therein. The liquid seal chamber 118 has a liquid 119 such as water, for example, therein at a selected level.

The cover 117 has a port 120 therein having a tube 121 extending therethrough and beneath the level of the liquid 119 in the liquid seal chamber 118. The tube 121 extends through a port 123 in the cover 112 to provide communication between the collection chamber 113 and the liquid seal chamber 118 whereby gases in the fluids from the pleural cavity of the patient, who is connected to the catheter 115', can flow from the collection chamber 113 through the tube 121 and the liquid 119 to the liquid seal chamber 118.

The gases are caused to flow to the liquid seal chamber 118 from the collection chamber 113 because of a vacuum pump 124 being connected by a tube 125 extending through a port 126 in the cover 117. Thus, the vacuum pump 124 exerts a negative pressure in the liquid seal chamber 118 with this being communicated to the pleural cavity of the patient connected to the catheter 115' through the collection chamber 113.

The negative pressure exerted by the vacuum pump 124 is controlled by a pressure regulating chamber 127, which is formed within a container 128 sealed by a cover 129. The pressure regulating chamber 127 has a liquid 130 such as water, for example, disposed therein to a selected level above the bottom of a tube 131, which communicates through a port 132 in the cover 129 with the atmosphere.

The cover 129 has a second port 134 therein connected to a port 135 in the cover 117 of the liquid seal container 116 by a tube 136. Thus, by controlling the level of the liquid 130 in the pressure regulating chamber 127, the pressure regulating chamber 127 controls the maximum negative pressure exerted by the vacuum pump 124.

The drainage apparatus 110 includes a container 140 having a cover 141 to seal the interior of the container 140 to form an excess negativity chamber 142. The excess negativity chamber 142 is connected with the collection chamber 112 by a tube 143 extending through a port 144 in the cover 141 and a port 145 in the cover 112.

The excess negativity chamber 142 has a tube 146 extending through a port 147 in the cover 141 for communication with the atmosphere. The bottom end of the tube 146 terminates above the bottom of the container 140.

The container 140 has a liquid 148 such as water, for example, disposed therein to a selected level greater than the level of the liquid 130 in the container 128. The level of the liquid 148 in the container 140 is selected so that the negative pressure within the pleural cavity of the patient, who is connected to the tube 115 by the catheter 115', will not exceed a predetermined or selected maximum above the negative pressure created in the pleural cavity of the patient by the vacuum pump 124. This is preferably about two centimeters of water greater than the negative pressure produced by the vacuum pump 124 in conjunction with the pressure regulating chamber 127. The vacuum pump 124, in conjunction with the pressure regulating chamber 127, produces a negative pressure in a range of twenty-five centimeters of water. With this preferred difference of two centimeters of water, the level of the liquid 148, when it is water, in the container 140 will be two centimeters greater than the level of the liquid 130, when it is water, in the container 128 as long as the bottoms of the tubes 131 and 146 are at the same level.

The drainage apparatus 110 includes a container 155 having a cover 156 to seal its interior to form an excess positive pressure chamber 157 therein. The cover 156 has a port 158 therein connected by a tube 159 to a port 160 in the cover 117 so that the excess positive pressure chamber 157 communicates with the liquid seal chamber 118.

The tube 159 extends from the port 158 in the cover 156 to a position below the level of a liquid 161, which may be water, for example, in the container 155. The cover 156 has a second port 162 therein to vent the excess positive pressure chamber 157 to the atmosphere through a tube 163.

Accordingly, if the pressure in the pleural cavity of the patient, the collection chamber 113, or the liquid seal chamber 118 should exceed a predetermined positive pressure, this positive pressure is vented through the excess positive pressure chamber 157 to the atmosphere by the tube 163 in the cover 156. The liquid 161 prevents any contamination of the drainage apparatus 110.

The drainage apparatus 110 does not use the flow control vent means 104 (see FIGS. 17 and 18) so that the excess negative pressure is dissipated as soon as possible rather than having the excess negative pressure removed in a predetermined period of time by a controlled flow rate of air through the flow control vent means 104. Except for the dissipation of the excess negative pressure as soon as possible, the drainage apparatus 110 (see FIG. 19) functions in the same manner as the drainage apparatus 10 (see FIG. 1). Thus, its operation will not be described.

The drainage apparatus 10 or 110 (see FIG. 19) is capable or ascertaining the negative pressure in the pleural cavity of a patient connected to the drainage apparatus 10 (see FIG. 1) or 110 (see FIG. 19). In the drainage apparatus 10 (see FIG. 1), this is accomplished by disconnecting the vacuum pump 47 and then measuring the difference in the two legs 99 and 101 with this difference being the negative pressure in the pleural cavity of the patient. In the drainage apparatus 110 (see FIG. 19), this is accomplished by disconnecting the vacuum pump 124 and measuring the increased level of the liquid in the tube 121 with this being the negative pressure in the pleural cavity of the patient.

While the present invention has shown and described each of the drainage apparatuses 10 (see FIG. 1) and 110 (see FIG. 19) as having a specific arrangement for releasing the excess positive pressure, it should be understood that any arrangement may be employed to release the positive pressure in each of the drainage apparatuses 10 (see FIG. 1) and 110 (see FIG. 19). Thus, any suitable means for releasing the excess positive pressure may be employed.

An advantage of this invention is that it enables control of the maximum excess negative pressure in the pleural cavity of a patient connected to the drainage apparatus. Another advantage of this invention is that it eliminates any possibility of the liquid seal being broken by the excess negative pressure. A further advantage of this invention is that the negative pressure in the pleural cavity of the patient can be measured.

For purposes of exemplification, particular embodiments of the invention have been shown and described according to the best present understanding thereof. However, it will be apparent that changes and modifications in the arrangement and construction of the parts thereof may be resorted to without departing from the spirit and scope of the invention.

I claim:

1. A drainage apparatus including:
    collection means having inlet means for communication with a pleural cavity of a body to receive fluids therefrom;
    vacuum means to create a first selected negative pressure within said collection means to normally maintain the pleural cavity communicating with said inlet means at the first selected negative pressure, said vacuum means removing from said collection means gases of the fluids received in said collection means from the pleural cavity communicating with said inlet means of said collection means;
    gas preventing return means between said collection means and said vacuum means to prevent return of gases to said collection means after being removed therefrom by said vacuum means;
    and control means to control the negative pressure within said collection means to a second selected higher negative pressure above the first selected negative pressure created by said vacuum means when the negative pressure within said collection means is increased.

2. The drainage apparatus according to claim 1 in which said control means includes means to admit atmospheric air to said collection means when the negative pressure within said collection means exceeds the second selected higher negative pressure above the first selected negative pressure to reduce the negative pressure within said collection means to the second selected higher negative pressure above the first selected negative pressure.

3. The drainage apparatus according to claim 2 including means to prevent the pressure in said collection means from exceeding a maximum positive pressure.

4. The drainage apparatus according to claim 3 in which said vacuum means includes:
    suction chamber means;
    passage means connecting said suction chamber means and said collection means;
    producing means connected to said suction chamber means to produce a negative pressure in said suction chamber means and said collection means;
    and means to control the negative pressure produced by said producing means in said suction chamber means and said collection means so that said collection means is normally maintained at the first selected negative pressure.

5. The drainage apparatus according to claim 1 in which said control means includes:
    communicating means to communicate said collection means with the atmosphere;
    and a liquid in said communicating means at a selected level to allow atmospheric air to flow through said communicating means to said collection means only when the negative pressure within said collection means exceeds the second selected higher above the negative pressure first selected negative pressure to reduce the negative pressure within said collection means.

6. The drainage apparatus according to claim 5 including means to prevent the pressure in said collection means from exceeding a maximum positive pressure.

7. The drainage apparatus according to claim 6 in which said vacuum means includes:
    suction chamber means;
    passage means connecting said suction chamber means and said collection means;
    producing means connected to said suction chamber means to produce a negative pressure in said suction chamber means and said collection means;
    and means to control the negative pressure produced by said producing means in said suction chamber means and said collection means so that said collection means is normally maintained at the first selected negative pressure.

8. The drainage apparatus according to claim 7 in which:
said control means of said vacuum means includes container means having a liquid therein at a selected level to control the negative pressure produced by said producing means;
and the selected level of liquid in said communicating means is above the selected level of liquid in said container means of said control means of said vacuum means in accordance with the amount that the second selected higher negative pressure is above the first selected negative pressure.

9. The drainage apparatus according to claim 1 in which said control means includes:
communicating means to communicate said collection means with the atmosphere;
and means to allow atmospheric air to flow through said communicating means to said collection means only when the negative pressure within said collection means exceeds the second selected higher above the negative pressure selected negative pressure to reduce the negative pressure within said collection means.

10. The drainage apparatus according to claim 9 including means to prevent the pressure in said collection means from exceeding a maximum positive pressure.

11. The drainage apparatus according to claim 10 in which said vacuum means includes:
suction chamber means;
passage means connecting said suction chamber means and said collection means;
producing means connected to said suction chamber means to produce a negative pressure in said suction chamber means and said collection means;
and means to control the negative pressure produced by said producing means in said suction chamber means and said collection means so that said collection means is normally maintained at the first selected negative pressure.

12. The drainage apparatus according to claim 1 in which said control means includes:
excess negativity chamber means;
first communicating means to communicate said excess negativity chamber means with said collection means;
second communicating means to communicate said excess negativity chamber means with the atmosphere;
and said excess negativity chamber means having a liquid therein at a selected level to enable atmospheric air to be introduced by said second communicating means through the liquid in said excess negativity chamber means to said collection means through said first communicating means when the negative pressure within said collection means exceeds the second selected higher negative pressure above the first selected negative pressure.

13. The drainage apparatus according to claim 12 including means to prevent the pressure in said collection means from exceeding a maximum positive pressure.

14. The drainage apparatus according to claim 13 in which said vacuum means includes:
suction chamber means;
passage means connecting said suction chamber means and said collection means;
producing means connected to said suction chamber means to produce a negative pressure in said suction chamber means and said collection means;
and means to control the negative pressure produced by said producing means in said suction chamber means and said collection means so that said collection means is normally maintained at the first selected negative pressure.

15. The drainage apparatus according to claim 14 in which:
said control means of said vacuum means includes container means having a liquid therein at a selected level to control the negative pressure produced by said producing means;
and the selected level of liquid in said excess negativity chamber means is above the selected level of liquid in said container means of said control means of said vacuum means in accordance with the amount that the second selected higher negative pressure is above the selected first negative pressure.

16. The drainage apparatus according to claim 1 in which said control means communicates with said collection means only on the side of said gas preventing return means communicating with said collection means.

17. The drainage apparatus according to claim 1 in which said control means is separate from said vacuum means.

18. The drainage apparatus according to claim 1 in which the second selected higher negative pressure is two centimeters of water above the first selected negative pressure.

19. The drainage apparatus according to claim 1 in which the difference between the second selected higher negative pressure and the first selected negative pressure is substantially smaller than the first selected negative pressure.

20. The drainage apparatus according to claim 1 in which the second selected higher negative pressure is only a slightly greater negative pressure than the first selected negative pressure.

* * * * *